(12) United States Patent
Nishimura et al.

(10) Patent No.: US 9,753,509 B2
(45) Date of Patent: Sep. 5, 2017

(54) IMAGING APPARATUS FOR THERMAL ANALYZER AND THERMAL ANALYZER INCLUDING THE SAME

(71) Applicant: Hitachi High-Tech Science Corporation, Minato-ku, Tokyo (JP)

(72) Inventors: Shinya Nishimura, Tokyo (JP); Hirohito Fujiwara, Tokyo (JP); Kentaro Yamada, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 208 days.

(21) Appl. No.: 14/606,345

(22) Filed: Jan. 27, 2015

(65) Prior Publication Data
US 2015/0264277 A1    Sep. 17, 2015

(30) Foreign Application Priority Data
Mar. 13, 2014  (JP) .................. 2014-049877

(51) Int. Cl.
| | | |
|---|---|---|
| G01N 25/00 | (2006.01) | |
| G06F 1/20 | (2006.01) | |
| H04N 5/225 | (2006.01) | |
| G01N 25/48 | (2006.01) | |
| G01N 5/04 | (2006.01) | |

(52) U.S. Cl.
CPC ........... *G06F 1/206* (2013.01); *H04N 5/2252* (2013.01); *H04N 5/2254* (2013.01); *G01N 5/04* (2013.01); *G01N 25/4853* (2013.01)

(58) Field of Classification Search
CPC ...... G01K 17/00; G06F 1/206; H04N 5/2254; C03B 5/005; F23M 11/04; F27D 2021/026; F27D 21/02

USPC ......... 348/83, 164; 374/10–14, 43; 702/130, 702/136; 110/185, 190, 235, 341, 346
See application file for complete search history.

(56) References Cited

U.S. PATENT DOCUMENTS

| | | | | |
|---|---|---|---|---|
| 4,695,881 | A | * 9/1987 | Kennedy | D21C 11/12 348/164 |
| 4,981,088 | A | * 1/1991 | Burris | F23J 3/00 110/182.5 |
| 5,834,661 | A | * 11/1998 | Nonaka | G01N 25/72 374/5 |

(Continued)

FOREIGN PATENT DOCUMENTS

JP    H02-102440    4/1990

*Primary Examiner* — Nathnael Aynalem
(74) *Attorney, Agent, or Firm* — Banner & Witcoff, Ltd.

(57) ABSTRACT

An imaging apparatus for a thermal analyzer is configured to image a heated sample inside a thermal analyzer main body section from an observation window provided in the thermal analyzer main body section. The imaging apparatus is provided with: an imaging device that is provided with a lens housing and a main body section; a holding section configured to hold the imaging device to have an orientation in which the lens housing is oriented toward the observation window, and the main body section is positioned on the opposite side of the observation window across the lens housing; and a cooling fan configured to provide airflow inside the holding section. The holding section is provided with a cooling air passage having an intake portion and an exhaust portion. At least a portion of the lens housing is arranged in the cooling air passage to be cooled by the airflow provided by the cooling fan.

6 Claims, 4 Drawing Sheets

(56) References Cited

U.S. PATENT DOCUMENTS

| | | | | |
|---|---|---|---|---|
| 6,111,599 | A * | 8/2000 | Nance | F27D 21/02 348/82 |
| 6,279,494 | B1 * | 8/2001 | Jimbo | C03B 5/005 110/185 |
| 6,325,621 | B1 * | 12/2001 | Murasaki | C03B 5/24 348/83 |
| 2005/0002435 | A1 * | 1/2005 | Hashimoto | G01N 25/72 374/43 |
| 2011/0069165 | A1 * | 3/2011 | Zombo | F01D 21/003 348/82 |
| 2012/0222683 | A1 * | 9/2012 | Lowe | A61F 6/225 128/831 |
| 2014/0113237 | A1 * | 4/2014 | Rohner | F27B 17/025 431/1 |

* cited by examiner

IMAGING APPARATUS FOR THERMAL ANALYZER AND THERMAL ANALYZER INCLUDING THE SAME

CROSS-REFERENCE TO RELATED APPLICATION

This application claims priority from Japanese Patent Application No. 2014-049877, filed on Mar. 13, 2014, the entire subject matter of which is incorporated herein by reference.

BACKGROUND

1. Technical Field

The present invention relates to an imaging apparatus for a thermal analyzer which images a heated sample inside a thermal analyzer from an observation window provided in the thermal analyzer and relates to a thermal analyzer provided with the imaging apparatus.

2. Description of the Related Art

Conventionally, as a method of evaluating temperature characteristics of a sample, there is known a method of a so-called thermal analysis in which a sample is heated and physical changes of the sample accompanied by temperature changes are measured. Thermal analysis is, for example, defined in JIS K 0129:2005 "Thermal Analysis General Rule" in which all the methods related to measuring physical characteristics of a sample while the temperature of a measurement target (sample) is controlled by a program are considered as thermal analysis. As a method of thermal analysis which is generally used, there are five methods, such as (1) a differential thermal analysis (DTA) for detecting a temperature (differential temperature), (2) a differential scanning calorimetry (DSC) for detecting a differential heat flow, (3) thermogravimetry (TG) for detecting mass (weight changes), (4) a thermo-mechanical analysis (TMA) for detecting dynamic characteristics, and (5) a dynamic mechanical analysis (DMA).

In the meantime, there have been requests hoping to observe a sample during thermal analysis, and therefore, there has been proposed a thermal analyzer that is provided with an observation window. As a technology of imaging a heated sample inside the thermal analyzer through the observation window, a thermal analyzer in which a telescope is installed facing the observation window and an optical axis from the telescope is bent to 90 degrees so as to be connected to a CCD camera has developed (cf. JP-A-2-1024440). According to the configuration disclosed in JP-A-2-1024440, since the CCD camera is arranged at a position apart from the high-temperature observation window in a vertical direction, it is possible to prevent the CCD camera from being damaged due to heat.

However, according to the configuration disclosed in JP-A-2-1024440, when an optical system such as a telescope or a mirror is arranged between an observation window (a sample therein) which is an imaging subject, and a camera so as to prohibit heat of the observation window from being directly applied to a camera lens, a distance between the sample and the lens increases. Generally, a distance between a sample S and a lens L is regulated by a working distance (operation distance) WD, and the WD is determined based on a magnitude of a viewing field V, a focal distance F of the lens, and a CCD size (size of an image on the CDD) I (cf. FIG. 2, which shows a configuration related to the present invention). Therefore, in order to arrange the optical system between the observation window and the camera, and to ensure resolution of an observation image of the sample S in a state where the WD is increased, the viewing field V may need to be constant. In this case, the focal distance F increases and a depth of field becomes shallow. Thus, fineness of the observation image is degraded with respect to irregularities of the sample S. In addition, the increased WD causes a disadvantage in that the configuration of the optical system increases in size or becomes complicated.

Moreover, when a camera is arranged above the observation window, if a transparent material (for example, quartz glass, heat resistant glass, and sapphire glass) is arranged therebetween for heat shielding, the transparent material and a furnace tube which is formed with a transparent material in a similar manner create a multi-layer, thereby causing a problem of a blurred observation image.

SUMMARY

The present invention has been made in view of the above-described circumstances, and one of objects of the present invention is to provide an imaging apparatus for a thermal analyzer in which a vivid image can be imaged without increasing the working distance between a sample and a lens and imaging apparatus is prevented from being damaged due to heat when imaging a heated sample inside a thermal analyzer through the observation window, and a thermal analyzer that is provided with the imaging apparatus for a thermal analyzer.

According to an exemplary embodiment of the present invention, there is provided an imaging apparatus for a thermal analyzer which images a heated sample inside a thermal analyzer main body section from an observation window provided in the thermal analyzer main body section. The imaging apparatus is provided with: an imaging device that is provided with a lens housing and a main body section; a holding section configured to hold the imaging device to have an orientation in which the lens housing is oriented toward the observation window, and the main body section is positioned on the opposite side of the observation window across the lens housing; and a cooling fan configured to provide airflow inside the holding section. The holding section is provided with a cooling air passage having an intake portion and an exhaust portion. At least a portion of the lens housing is arranged in the cooling air passage to be cooled by the airflow provided by the cooling fan.

According to another exemplary embodiment of the present invention, there is provided a thermal analyzer that is provided with: a thermal analyzer main body section that is provided with an observation window through which a heated sample arranged inside the thermal analyzer main body is imaged; and an imaging apparatus. The imaging apparatus is provided with: an imaging device that is provided with a lens housing and a main body section; a holding section configured to hold the imaging device to have an orientation in which the lens housing is oriented toward the observation window, and the main body section is positioned on the opposite side of the observation window across the lens housing; and a cooling fan configured to provide airflow inside the holding section. The holding section is provided with a cooling air passage having an intake portion and an exhaust portion. At least a portion of the lens housing is arranged in the cooling air passage to be cooled by the airflow provided by the cooling fan.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Hereinafter, embodiments of the present invention will be described with reference to the drawings.

Figure 1:
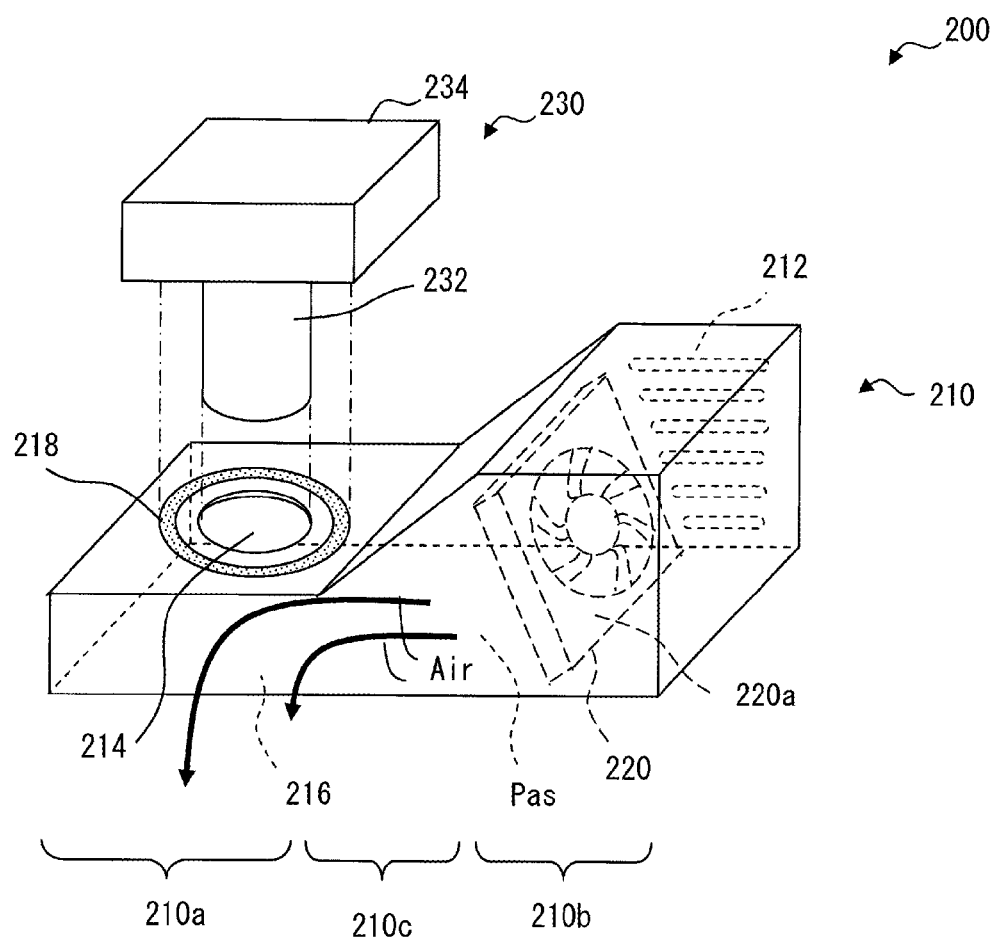
FIG. 1 is a perspective view illustrating a schematic configuration of an imaging apparatus for a thermal analyzer according to a first embodiment of the present invention.

FIG. 1 is a perspective view illustrating a schematic configuration of an imaging apparatus 200 for a thermal analyzer according to a first embodiment of the present invention. The imaging apparatus 200 for a thermal analyzer includes imaging device 230 that is provided with a lens housing 232 and a main body section 234, a holding section 210 that holds the imaging device 230, and a cooling fan 220 arranged inside the holding section 210. In FIG. 1, illustrations for below-described illumination device 240, stand 260 (refer to FIG. 2) and the like are omitted.

In the imaging device 230 to be described later in detail, the lens housing 232 is oriented directly toward an observation window of a thermal analyzer main body section, and the imaging device 230 is held by the holding section 210 so as to cause the main body section 234 to be positioned on the opposite side of the observation window across the lens housing 232. The imaging device 230 is configured by a CCD camera or a digital video camera, for example, and is capable of imaging a heated sample inside a thermal analyzer main body section 150, which is described later. One or more lenses are built into the lens housing 232, and the main body section 234 has imaging elements such as CCD elements, or various control units.

Along a lateral direction in FIG. 1, a left-side portion 210a of the holding section 210 is substantially box-shaped having a predetermined height and connected to an intermediate portion 210c. The intermediate portion 210c forms a trapezoid-shaped box which is obliquely erected toward the right side and is connected integrally to a substantially box-shaped right-side portion 210b having a predetermined height higher than the left-side portion 210a. In addition, all the bottom surfaces in the holding section 210 (the bottom surface of each of the left-side portion 210a, the right-side portion 210b, and the intermediate portion 210c) are open, and the left-side part from the below-described cooling fan 220 in FIG. 1 out of the bottom surfaces forms an exhaust portion 216. The holding section 210 cam be formed by performing pressing or the like of a steel plate, for example.

The cooling fan 220 is arranged in the inner space of the right-side portion 210b, and an intake surface 220a of the cooling fan 220 is oriented from the left side toward the right side in FIG. 1 in an erected manner. In addition, in the right-side portion 210b, a plurality of slits are open on two side surfaces on the right side from the intake surface 220a of the cooling fan 220, thereby forming an intake portion 212 (in FIG. 1, only the intake portion 212 on one side is illustrated). Then, the inner space of the holding section 210 between the intake portion 212 and the exhaust portion 216 forms a cooling air passage Pas, and a cooling air Air supplied from the cooling fan 220 passes along the cooling air passage Pas.

In a top surface of the left-side portion 210a in the holding section 210, a circular opening portion 214 having a diameter slightly greater than that of the lens housing 232 is formed, and the cylindrical lens housing 232 can be inserted into the cooling air passage Pas inside the left-side portion 210a through the opening portion 214. In addition, in the top surface of the left-side portion 210a, a ring-shaped magnet 218 is arranged on an outer peripheral side of the opening portion 214. When the lens housing 232 of the imaging device 230 is inserted into the opening portion 214, the bottom surface of the main body section 234 having a diameter greater than that of the lens housing 232 abuts on the magnet 218, and thus, the main body section 234 can be fixed to the top surface of the left-side portion 210a by the magnet 218. The main body section 234 has a housing formed with a ferromagnetic material such as a steel plate which is attracted by a magnet.

As described above, the imaging device 230 is fixed to (held by) the holding section 210, and a tip end side of the lens housing 232 protrudes to the bottom surface side from the exhaust portion 216. The method of fixing the imaging device 230 is not limited to the magnet.

Subsequently, with reference to FIG. 2, a configuration of a thermal analyzer 300 that is provided with the imaging apparatus 200 and a thermal analyzer main body section 150 will be described.

The imaging apparatus 200 for a thermal analyzer has the illumination device 240 and the stand 260 in addition to the above-described holding section 210. The illumination device 240 has a ring shape which surrounds an outer periphery of the lens housing 232 further protruding to the bottom surface side than the exhaust portion 216 and installed in a lower portion of the holding section 210 by a plurality of installation stays 250 extending downward from a side surface of the holding section 210. The illumination device 240 is configured by an LED light, for example.

The stand 260 is provided with a strut 261 which vertically extends, an installation member 262 which is installed in the right-side portion 210b of the holding section 210, and a base portion 264 which is placed on a ground contact surface. The installation member 262 can be freely fixed to a predetermined position of the strut 261. Therefore, a position of the imaging device 230 in a height direction on the thermal analyzer main body section 150 can be adjusted by adjusting a position of the installation member 262 to be fixed.

Meanwhile, the thermal analyzer main body section 150 is an actual measurement device including a thermal analyzer section 100 to perform a thermal analysis. The thermal analyzer main body section 150 has an observation window W and can image a heated sample S inside the thermal analyzer section 100 through the observation window W.

Figure 2:
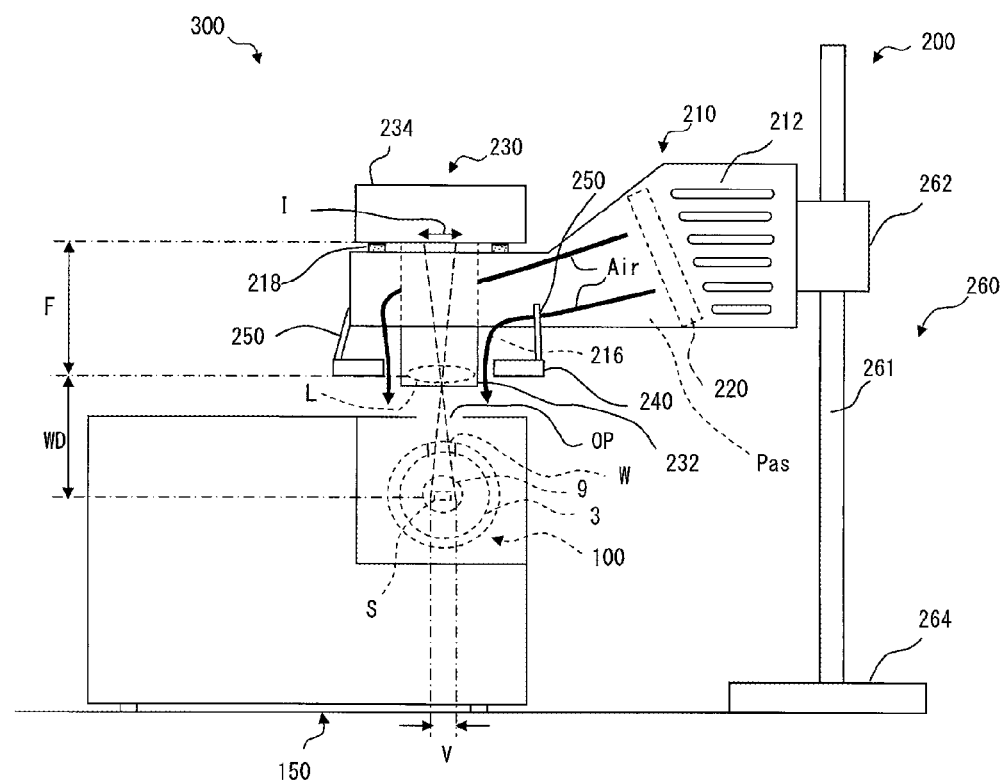
FIG. 2 is a diagram illustrating a configuration of a thermal analyzer provided with the imaging apparatus and a thermal analyzer main body section.
Figure 3:
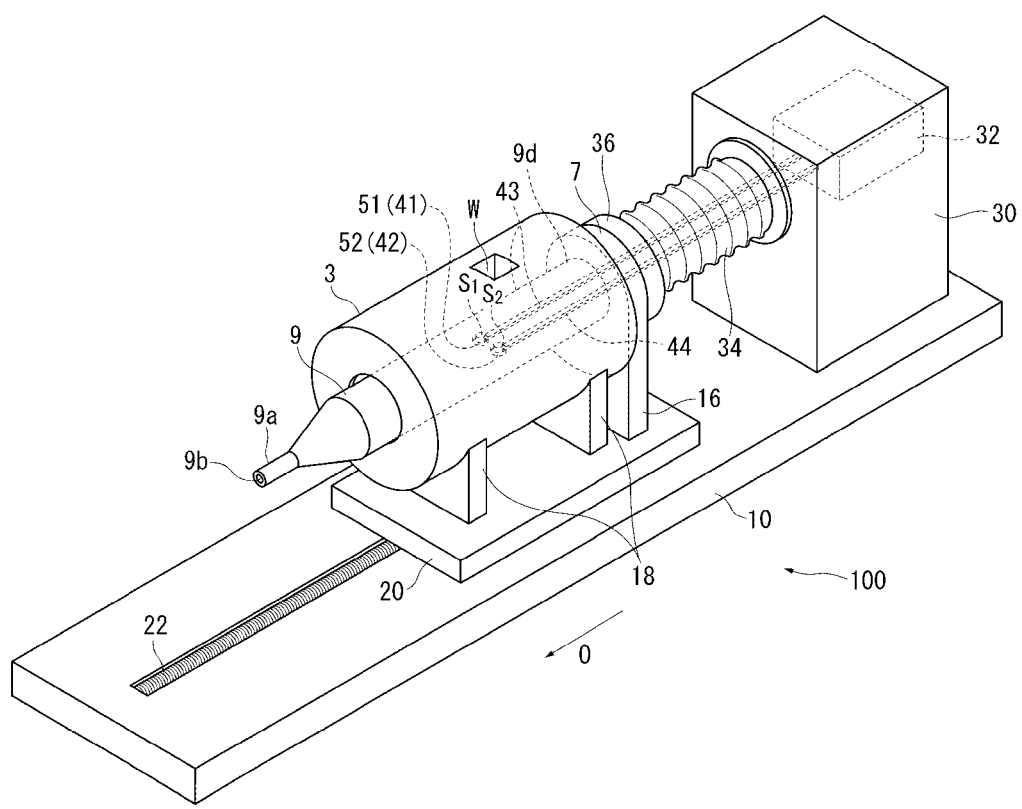
FIG. 3 is a perspective view illustrating a configuration of a thermal analyzer section of the thermal analyzer.

As illustrated in FIG. 3, the thermal analyzer section 100 is configured to be a thermogravimetry (TG) device and has a transparent tube-shaped furnace tube 9, a tube-shaped heating furnace 3 which surrounds the furnace tube 9 from outside, and a pair of sample holders 41 and 42 arranged inside the furnace tube 9. Then, the observation window W is open on a top surface of the heating furnace 3 so that samples S1 and S2 (In FIG. 2, collectively indicated as "S") mounted on the sample holders 41 and 42 inside the transparent furnace tube 9 are imaged from above the observation window W.

Here, the measurement sample (sample) $S_1$ and the reference sample $S_2$ are respectively accommodated in a pair of sample containers 51 and 52, and the sample containers 51 and 52 are respectively placed on the pair of the sample holders 41 and 42. Moreover, the sample holders 41 and 42 are respectively connected to balance arms 43 and 44 horizontally extending together. In addition, a thermocouple is installed immediately under the sample holders 41 and 42 so as to be able to measure the temperatures of the samples.

The reference sample $S_2$ is a reference substance (reference) with respect to the measurement sample. In the present invention, any of the measurement sample $S_1$ and the reference sample $S_2$ may be imaged and both the measurement sample $S_1$ and the reference sample $S_2$ correspond to the claimed "sample" in the present application.

The furnace tube 9 is formed with a transparent material such as quartz glass, sapphire glass, and yttrium aluminum garnet (YAG) ceramics.

The furnace tube 9 decreases in diameter so as to be tapered toward a tip end portion 9a. The tip end portion 9a is formed to have an elongated capillary shape, and an exhaust portion 9b is open at the tip end thereof. Then, purge gas is appropriately introduced from the rear end side to the furnace tube 9, and decomposition products and the like of a sample due to the purge gas or heating are discharged to the outside through the exhaust portion 9b.

Two struts 18 respectively extend downward from the lower end in the vicinity of both ends of the heating furnace 3 in an axial direction. Each of the struts 18 is connected to a top surface of a support plate 20. In addition, a flange portion 7 is fixed to the outside a rear end portion 9d of the furnace tube 9, and one strut 16 extends downward from the lower end of the flange portion 7. The strut 16 is connected to the top surface of the support plate 20.

A measurement chamber 30 is connected to the rear end portion 9d of the furnace tube 9 in an axial direction O. In the measurement chamber 30, a weight detector 32 which measures each weight of the samples $S_1$ and $S_2$ at the tip ends of the balance arms 43 and 44 is arranged. In addition, a tube-shaped bellows 34 is installed in the tip end portion of the measurement chamber 30, and the bellows 34 on the tip end side forms a flange portion 36.

Then, the support plate 20 and the measurement chamber 30 are placed on the top surface of a base 10. Moreover, an actuator 22 is arranged in a groove formed along the base 10 in the axial direction O, and the support plate 20 is allowed to move back and forth in the axial direction O along the groove by the actuator 22. Then, the support plate 20 retreats toward the measurement chamber 30, and the flange portion 36 is air-tightly connected to the flange portion 7. The insides of the measurement chamber 30 and the furnace tube 9 communicate with each other, and the rear end of each of the balance arms 43 and 44 extends to the inside of the measurement chamber 30 through the furnace tube 9.

The observation window W is positioned immediately above the sample containers 51 and 52 (the sample holders 41 and 42) so as to perform the measurement of the thermal analysis. In the top surface of the housing of the thermal analyzer main body section 150, an opening OP is formed in a portion including the observation window W, thereby imaging the sample S during thermal analysis through the opening OP.

When the samples $S_1$ and $S_2$ are set or replaced, the support plate 20 in its entirety of the furnace tube 9 is moved forward to the tip end side, and each of the sample holders 41 and 42 is exposed on the rear end side from the furnace tube 9 and the heating furnace 3.

Subsequently, an operation of the imaging apparatus 200 for a thermal analyzer of the embodiment of the present invention will be described.

As illustrated in FIG. 2, the lens housing 232 of the imaging apparatus 200 for a thermal analyzer is arranged immediately above the observation window W so as to cause the lens housing 232 to be oriented directly toward the observation window W. In this case, since there is no optical system such as a telescope or a prism to be interposed between the lens L and the sample S in the lens housing 232, a vivid image of the sample S can be obtained without increasing the WD or making the optical system increased in size or complicated.

In addition, by supplying the cooling air Air along the cooling air passage Pas from a cooling fan 220 of the imaging apparatus 200 for a thermal analyzer, the lens housing 232 of which at least a portion is arranged in the cooling air passage Pas is cooled by the cooling air Air. Accordingly, when the lens housing 232 is installed so as to be oriented directly toward the observation window W, heat of the high-temperature observation window W is prohibited from being transferred to the lens housing 232, and the imaging device 230 is prevented from being damaged due to heat.

Particularly, in the present embodiment, the tip end side of the lens housing 232 further protrudes to the bottom surface side than the exhaust portion 216. Then, the exhaust portion 216 surrounds the outside of the lens housing 232 in the circumferential direction and is open toward the tip end side of the lens housing 232 in the axial direction and toward the observation window W.

Therefore, as illustrated in FIG. 2, the cooling air Air is discharged from the exhaust portion 216 to the tip end side of the lens housing 232 in the axial direction. In this case, since the cooling air Air flows along the lens housing 232, even though the tip end side of the lens housing 232 protrudes from the exhaust portion 216, the lens housing 232 can be more securely cooled. Since the cooling air Air flows in a direction so as to keep heat of the high-temperature observation window W away from the lens housing 232, the cooling effect is further improved.

In addition, in the embodiment, the left-side portion 210a of the holding section 210 has the lowest height, and the height increases from the intermediate portion 210c toward the right-side portion 210b. Then, the exhaust portion 216 is formed in the left-side portion 210a, and the intake portion 212 is formed in the right-side portion 210b.

For this reason, the cooling air passage Pas becomes narrower from the intake portion 212 toward the exhaust portion 216, that is, a cross-sectional area of the cooling air passage Pas decreases. Accordingly, a flow rate in the cooling air passage Pas increases in the vicinity of the exhaust portion 216. Then, since the lens housing 232 is arranged on a side closer to the exhaust portion 216 than the intake portion 212, the flow rate of cooling air flowing in the lens housing 232 through the cooling air passage Pas increases. Thus, the cooling effect is further improved.

The expression "the lens housing 232 is arranged on a side closer to the exhaust portion 216 than the intake portion 212" denotes that the shortest distance between the lens housing 232 and the exhaust portion 216 is shorter than the shortest distance between the lens housing 232 and the intake portion 212.

Figure 4:
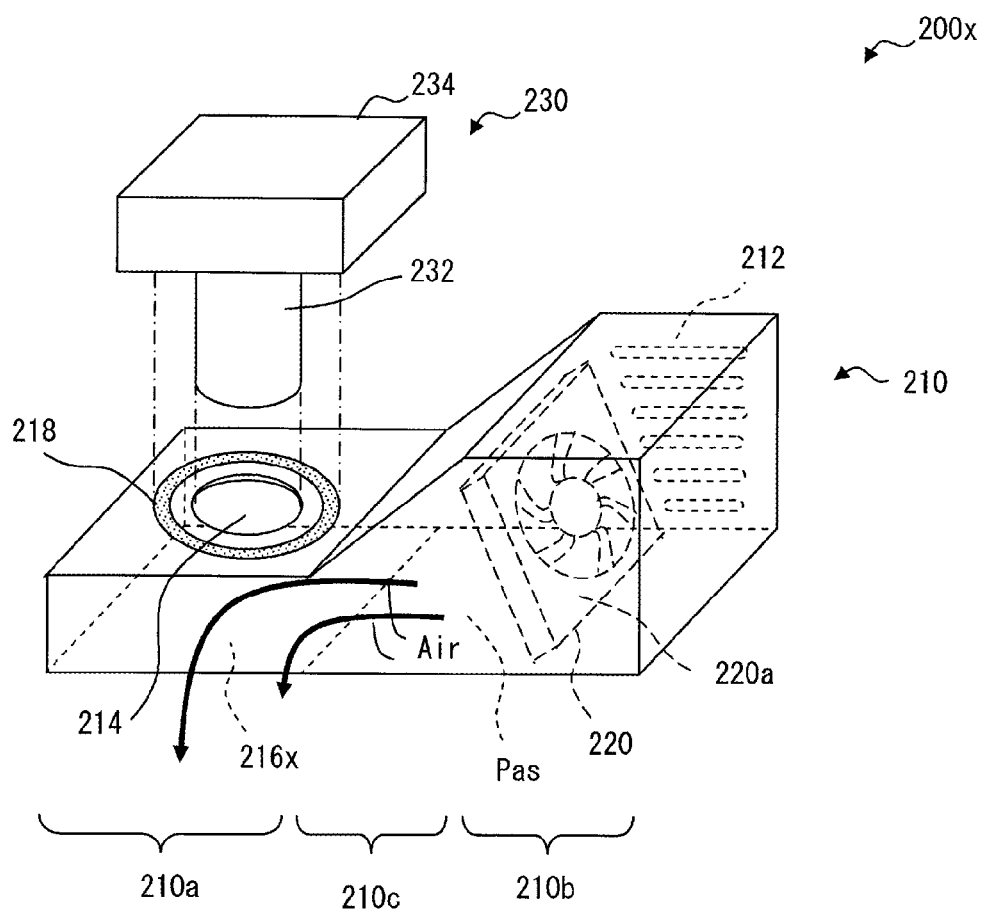
FIG. 4 is a perspective view illustrating a schematic configuration of the imaging apparatus for a thermal analyzer according to a second embodiment of the present invention.

Subsequently, with reference to FIG. 4, the imaging apparatus for a thermal analyzer according to the second embodiment of the present invention will be described. FIG.

4 is a perspective view illustrating a schematic configuration of an imaging apparatus 200x for a thermal analyzer of the second embodiment.

The imaging apparatus 200x for a thermal analyzer has a bottom plate on the bottom surface of the holding section 210. However, the bottom surface of the left-side portion 210a is open so as to form an exhaust portion (exhaust port) 216x, which makes a difference with respect to the first embodiment. It is not necessary to mention that the imaging apparatus 200x for a thermal analyzer also exhibits an operational effect similar to that of the imaging apparatus 200 for a thermal analyzer.

It is not necessary to mention that the present invention is not limited to the embodiments described above and includes various changes, modifications and equivalents within the spirit and scope of the present invention.

For example, in addition to the above-described thermogravimetry (TG) device, the thermal analyzer main body section can be applied to other types of thermal analysis including all of the thermal analysis that is defined in JIS K 0129:2005 "Thermal Analysis General Rule" and measures physical characteristics of a sample at the time of controlling temperatures of a measurement target (sample) by a program. Specifically, (1) a differential thermal analysis (DTA) for detecting a temperature (differential temperature), (2) a differential scanning calorimetry (DSC) for detecting a differential heat flow, (3) thermogravimetry (TG) for detecting mass (weight changes), and the like can be exemplified. The thermal analyzer main body section 150 is not limited to a type including the above-described furnace tube. In addition, the shape, size, position, and the like of the opening portion 214 are not limited to the above-described examples.

The shape of the holding section 210, the number of the cooling fans 220, and the shape or the numbers of the exhaust portion 216 and the cooling air passage Pas are not limited to the above-described examples.

The illumination device 240 may be fixed to an arm (not illustrated) which is connected directly to the stand 260.

It is acceptable as long as a portion of the lens housing 232 is arranged in the cooling air passage Pas. However, the lens housing 232 in its entirety may be arranged in the cooling air passage Pas. In addition, in the embodiment, the main body section 234 of the imaging apparatus 200 is arranged above the holding section 210 and is not arranged in the cooling air passage Pas. However, at least a portion of the main body section 234 may be arranged in the cooling air passage Pas. Since the main body section 234 of the imaging apparatus 200 is positioned on the opposite side of the observation window W across the lens housing 232, even though the main body section 234 is not arranged in the cooling air passage Pas, the main body section 234 is not further heated than the lens housing 232.

What is claimed is:

1. An imaging apparatus for a thermal analyzer which images a heated sample inside a thermal analyzer main body section from an observation window provided in the thermal analyzer main body section, the imaging apparatus comprising:
    an imaging device that is provided with a lens housing and a main body section;
    a holding section configured to hold the imaging device to have an orientation in which the lens housing is oriented toward the observation window, and the main body section is positioned on an opposite side of the observation window across the lens housing; and
    a cooling fan configured to provide airflow inside the holding section,
    wherein the holding section is provided with a cooling air passage having an intake portion and an exhaust portion,
    wherein at least a portion of the lens housing is arranged in the cooling air passage to be cooled by the airflow provided by the cooling fan, and
    wherein the exhaust portion is opened toward a tip end side of the lens housing in an axial direction and toward the observation window so as to surround outer circumference of the lens housing, and cooling air is discharged from the exhaust portion to the tip end side of the lens housing in the axial direction.

2. The imaging apparatus according to claim 1, wherein the cooling fan is arranged inside the holding section.

3. The imaging apparatus according to claim 1, wherein the cooling air passage is configured to have a cross-sectional area that decreases from the intake portion toward the exhaust portion, and the lens housing is arranged on a side closer to the exhaust portion than the intake portion.

4. A thermal analyzer comprising:
    a thermal analyzer main body having a section that is provided with an observation window through which a heated sample arranged inside the thermal analyzer main body is imaged; and
    an imaging apparatus comprising:
        an imaging device that is provided with a lens housing and a main body section;
        a holding section configured to hold the imaging device to have an orientation in which the lens housing is oriented toward the observation window, and the main body section is positioned on an opposite side of the observation window across the lens housing; and
        a cooling fan configured to provide airflow inside the holding section,
    wherein the holding section is provided with a cooling air passage having an intake portion and an exhaust portion,
    wherein at least a portion of the lens housing is arranged in the cooling air passage to be cooled by the airflow provided by the cooling fan, and
    wherein the exhaust portion is opened toward a tip end side of the lens housing in an axial direction and toward the observation window so as to surround outer circumference of the lens housing, and cooling air is discharged from the exhaust portion to the tip end side of the lens housing in the axial direction.

5. The thermal analyzer according to claim 4, wherein the cooling fan is arranged inside the holding section.

6. The thermal analyzer according to claim 4, wherein the cooling air passage is configured to have a cross-sectional area that decreases from the intake portion toward the exhaust portion, and the lens housing is arranged on a side closer to the exhaust portion than the intake portion.

* * * * *